United States Patent [19]

Broomé

[11] Patent Number: 5,207,694
[45] Date of Patent: May 4, 1993

[54] METHOD FOR PERFORMING A SURGICAL OCCLUSION, AND KIT AND APPLICATOR FOR CARRYING OUT THE METHOD

[75] Inventor: Albert Broomé, Helsingborg, Sweden

[73] Assignee: Surgical Invent AB, Helsingborg, Sweden

[21] Appl. No.: 900,425

[22] Filed: Jun. 18, 1992

[51] Int. Cl.$^5$ .............................................. A61B 17/00
[52] U.S. Cl. ........................................ 606/148; 606/1; 606/151; 606/228; 24/46 PB
[58] Field of Search ................. 606/1, 139, 140, 144, 606/148, 150, 151, 157, 158, 187, 228, 110–113; 24/16 PB, 305 P

[56] References Cited

U.S. PATENT DOCUMENTS

| | | | |
|---|---|---|---|
| 3,570,497 | 3/1971 | Lemole | 128/335.5 |
| 3,576,054 | 4/1971 | Rynk | 24/16 |
| 3,588,963 | 6/1971 | Moberg | 24/16 PB |
| 3,926,193 | 12/1975 | Hasson | 128/335 |
| 3,971,384 | 7/1976 | Hasson | 128/335 |
| 4,119,091 | 10/1978 | Partridge | 128/92 B |
| 4,307,903 | 12/1981 | Wallace | 285/114 |
| 4,516,293 | 5/1985 | Beran | 24/16 PB |
| 4,592,355 | 6/1986 | Antebi | 128/326 |
| 4,667,662 | 5/1987 | Titone et al. | 128/92 YD |
| 4,730,615 | 3/1988 | Sutherland et al. | 128/335 |
| 4,760,846 | 8/1988 | Mers Kelly et al. | 128/327 |
| 4,784,139 | 11/1988 | Demos | 606/148 |
| 4,813,416 | 3/1989 | Pollak et al. | 128/335 |
| 4,955,913 | 9/1990 | Robinson | 606/228 |
| 5,112,344 | 5/1992 | Petros | 606/144 |
| 5,123,913 | 6/1992 | Wilk et al. | 606/151 |

Primary Examiner—Stephen C. Pellegrino
Assistant Examiner—Glenn Dawson
Attorney, Agent, or Firm—Kane, Dalsimer, Sullivan, Kurucz, Levy, Eisele and Richard

[57] ABSTRACT

A method, a kit and an applicator for performing a surgical occlusion. A tubular applicator open at both ends is introduced with a first end adjacent a free-prepared tissue. At least one bundle-strap type tie is introduced into the applicator. A tie portion protruding from said first end of the applicator is caught in order to position the tie in its proper place around the tissue. Thereafter, the tie is formed into a locked occlusion loop around said tissue. The occlusion technique is applicable to both laparotomy and laparoscopy.

22 Claims, 10 Drawing Sheets

METHOD FOR PERFORMING A SURGICAL OCCLUSION, AND KIT AND APPLICATOR FOR CARRYING OUT THE METHOD

BACKGROUND OF THE INVENTION

The present invention relates to a method, a kit and an applicator for performing a surgical occlusion on a human or animal body. More particularly, in accordance with the invention use is made e.g. of elongated and flexible, bundle-strap type occlusion ties which are passed and locked into occlusion loops around a tissue.

A surgical operation (on a human or animal body) frequently involves the sectioning of tissues containing vessels. For example, such sectioning is necessary in order to remove organs, or parts thereof, from the body. If the tissue to be sectioned is thin and superficial and the vessels are correspondingly small, sectioning normally does not involve any difficulties when employing conventional ligation/occlusion techniques.

Generally, present-day sectioning and occlusion techniques comprise the following two alternative procedures. According to the first alternative, one or more ligatures are applied on each side of the intended sectioning area, whereupon the tissue is sectioned. According to the second alternative, two pairs of pair of tissue forceps are initially applied at a certain mutual distance over the intended sectioning area, whereupon the tissue is sectioned between the forceps, and a ligature is performed on the opposite side of the respective forceps, which are then finally removed.

Normally, a ligature is a suture thread which is applied around the tissue and knotted to establish a firm seal or occlusion. When a suture is to be applied around a free-prepared non-sectioned tissue, a pair of curved pliers is first introduced under the tissue from one side. At the other side of the tissue, the pliers are opened to grasp one end of a suture thread which by some other means, such as a pair of tissue forceps, has been introduced into the operation area. The pliers are then withdrawn, taking with them the suture thread which thus remains in its proper place around the tissue. Such application of the suture thread has to be performed with great care so as not to damage the tissue and adjacent organs. After the suture thread thus has been positioned around the tissue, the actual knotting is performed, the first knot accomplishing a sealing function and the succeeding knots accomplishing a locking function. This procedure of applying and locking a suture thread has to be repeated for each ligature, i.e. at least twice. Ligation outside a pair forceps on a non-sectioned tissue is performed in practically the same way.

However, when the operation is performed in a deep and narrow area, it is sometimes difficult and troublesome to introduce the suture around the tissue and establish a firm and secure ligature. One reason could be that the suture is not sufficiently tightened before knotting. Also, the knot itself could be insufficiently strong and thus come loose, so that the ligature slides off, involving a risk of peroperative or postoperative bleeding. If bleeding occurs during the operation, a hemostatic instrument has to be applied more or less blindly with a risk of damaging organs. A postoperative sliding-off of a ligature may necessitate a further and difficult operation.

U.S. Pat. No. 4 955 913 discloses a bundle-strap type, one-piece surgical tie including a retaining head from which a tongue extends. The tongue is to be inserted into the retaining head so as to form a loop around living tissue and ligate such tissue, especially during the performance of feline and canine hysterectomies. The retaining head includes locking means for receiving the tongue and retaining it against a loop-opening movement. The tongue is formed as an elongated and flexible flat member having a smooth outer side and a toothed opposite side for engaging the locking means of the retaining head. The document does not disclose any special technique for applying the ties.

SUMMARY OF THE INVENTION

It is a general object of the present invention to provide a novel technique for performing a surgical occlusion, which overcomes the difficulties of prior-art techniques.

It is a more particular object of the present invention to provide a novel technique for performing a surgical occlusion in such deep and narrow areas where it may be difficult to apply a firm occlusion with present-day techniques.

It is yet another object of the present invention to provide a novel technique for expediently performing a firm and secure surgical occlusion, without any substantial risk of damaging adjacent organs.

It is a specific object of the invention, according to a first aspect thereof, to provide a novel technique for performing a surgical occlusion during laparotomy or thoracotomy.

It is another specific object of the invention, according to a second aspect thereof, to provide a novel technique for performing a surgical occlusion during laparoscopy.

According to the invention, these and other objects are achieved by a method, a kit and an applicator as set forth in the appended claims.

BRIEF DESCRIPTION OF THE DRAWINGS

Other features and advantages of the present invention, in addition to those mentioned above, will become apparent from the following detailed description of examples of carrying out the invention, in conjunction with the accompanying drawings which schematically disclose, by way of example, the principles of the invention, and the best mode which have been contemplated for carrying them out.

In the drawings:

FIG. 8a is a broken-away view showing on an enlarged scale an end portion of said applicator.

DESCRIPTION OF PREFERRED EMBODIMENTS

Figure 1:
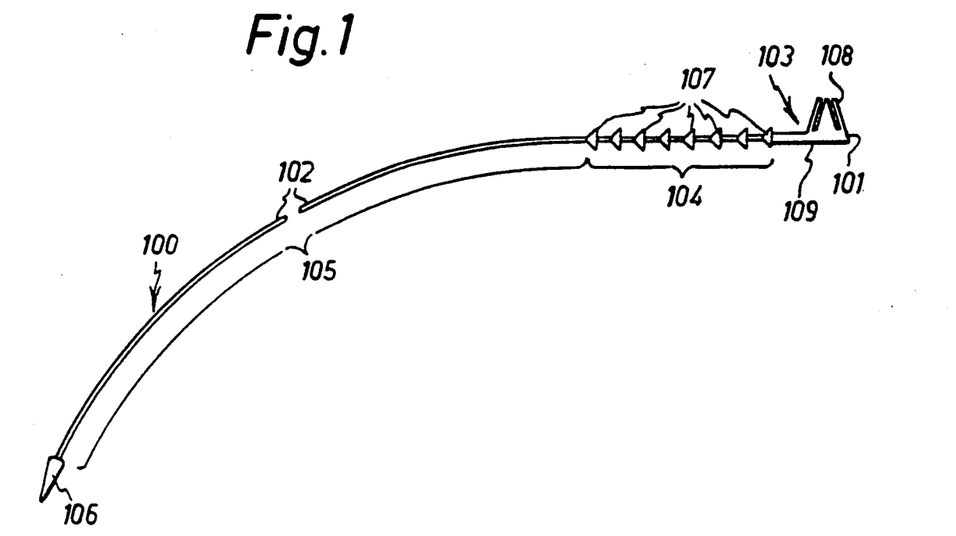
FIG. 1 is a perspective view of an exemplifying occlusion tie.
Figure 2:
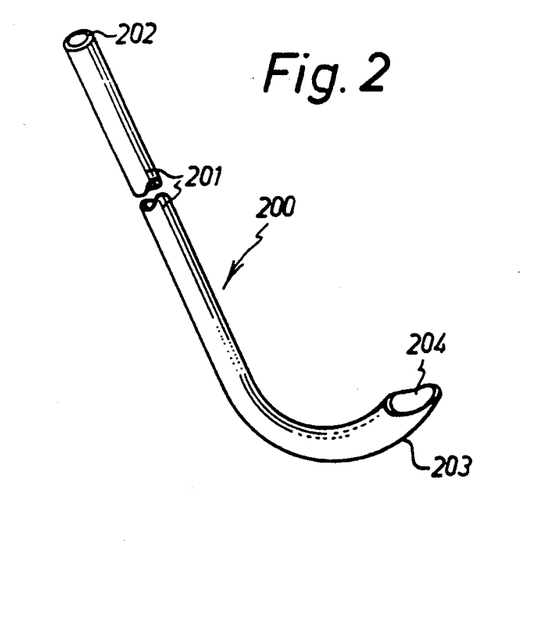
FIG. 2 is a perspective view of an exemplifying tie applicator for use in laparotomy.
Figure 7:
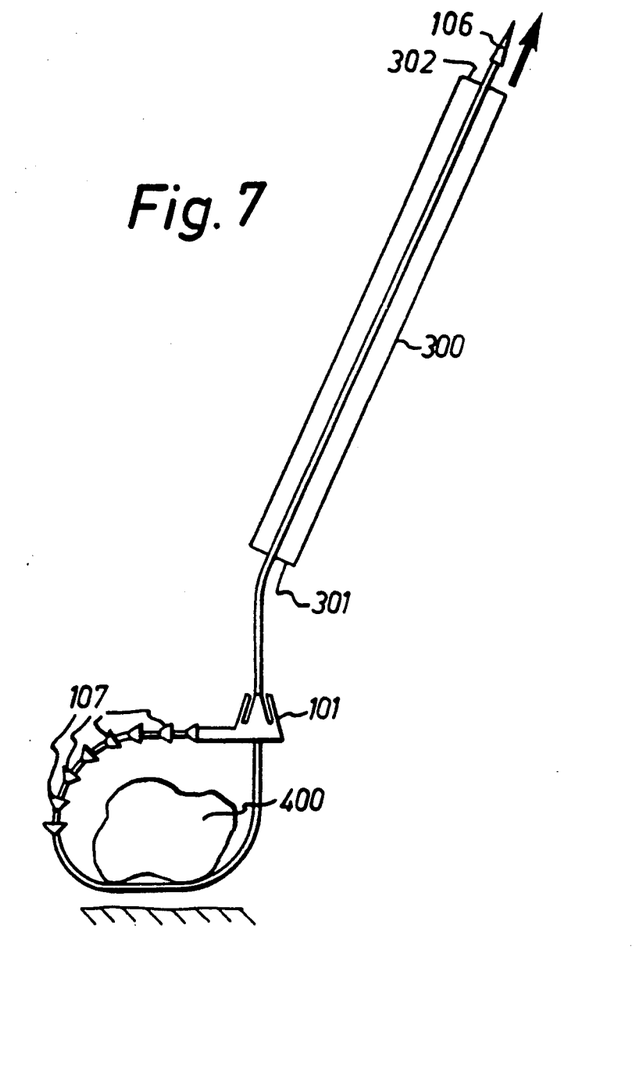

Turning now to FIGS. 1 and 2, an occlusion kit in accordance with a first aspect of the invention for use in laparotomy (or thoracotomy) basically includes one or more bundle-strap type occlusion ties 100 (FIG. 1), and an applicator 200 for said ties 100 (FIG. 2). Optionally, the kit also includes a loop-tightening device 300 (FIG. 7).

Referring to FIG. 1, a preferred embodiment of an occlusion tie 100, for use in either laparotomy or in laparoscopy in order to perform an occlusion according to the invention, comprises an elongated, flexible strap having an apertured retaining head 101 and a tongue 102 which extends from the retaining head 101 and is formed integrally therewith. Starting from the retaining head 101, the tongue 102 comprises a relatively short head portion 103, an intermediary portion 104, a relatively long tail portion 105 and an insertion tip 106. The intermediary portion 104 is provided with a row of eight spaced-apart locking cones 107 tapering towards the insertion tip 106. The head portion 103 and the tail portion 105 of the tongue 102 are not provided with such locking cones.

The retaining head 101 is generally frustoconical in shape, and includes four upright, resilient locking fingers 108 defining a central opening 109 for receiving the tongue 102.

The locking cones 107 located on the intermediary portion 104 of the tongue 102 are intended to engage and cooperate with the locking fingers 108 when the tongue 102 is inserted into and pulled through the central opening 109 of the retaining head 101, whereby the tie 100 is formed into a locked occlusion loop.

According to a preferred embodiment, the tie 100 has an overall length of about 350 mm, and is substantially thread-shaped and circular in cross-section, so as to be flexible in all directions relative to the main axis of the tongue 102. The diameter of the tongue 102 may be about 0.5 mm. The tie 100 can be made in one piece from a non-resorbable material, such as polypropylene, or a resorbable material, such as polydiaoxanone. The locking cones 107 may have a diameter of about 1.8 mm and be arranged at a mutual distance of about 3 mm. The head portion 103 of the tongue 102 may be about 7 mm. The tail portion 105 of the tongue 102 may optionally have a slightly increased diameter, e.g. 1.0 mm, compared with the head portion 103 and the intermediary portion 104.

Laparotomy

Referring now to FIG. 2, the applicator 200 for use in laparotomy consists of a substantially J-shaped tube having a long leg 201 with an open end 202, and a short leg 203 with an open end 204. The applicator 200 is dimensioned so as to allow a tie 100, including its retaining head 101, to be passed completely through the applicator 200. Preferably, the J-shaped applicator 200 for use in laparotomy is dimensioned so as to allow a plurality of ties 100 to be passed completely and substantially simultaneously through the applicator.

As indicated in FIG. 2, the short leg end 204 of the applicator 200 is preferably obliquely cut and spoon-shaped. The overall length of the applicator 200 is less than that of the ties 100. With ties 100 having a length of 350 mm, the length of the applicator 200 can be 250 mm.

The applicator 200 can be made of any suitable material, such as plastic (PVC).

Turning now to FIGS. 3–7, successive method steps for performing an occlusion during laparotomy using ties 100 as shown in FIG. 1 and a J-shaped applicator 200 as shown in FIG. 2 are schematically illustrated.

Figure 3:
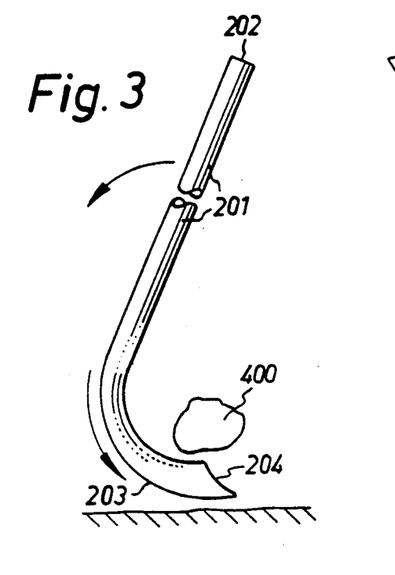
FIGS. 3–7 are simplified views, schematically illustrating successive steps taken during the performance of an occlusion around a tissue during laparotomy, using ties as shown in FIG. 1, an applicator as shown in FIG. 2, and optionally a tightening tube 300 as shown in FIG. 7.

After performing a free-preparation of a tissue 400 to be occluded and sectioned, the J-shaped applicator 200 is introduced into the operation area by manually handling the long leg 201, the short leg 203 being passed under and around the free-prepared tissue 400, as shown in FIG. 3. The spoon-shape of the short leg end 204 of the applicator 200 will minimise damages to surrounding tissues.

Figure 4:
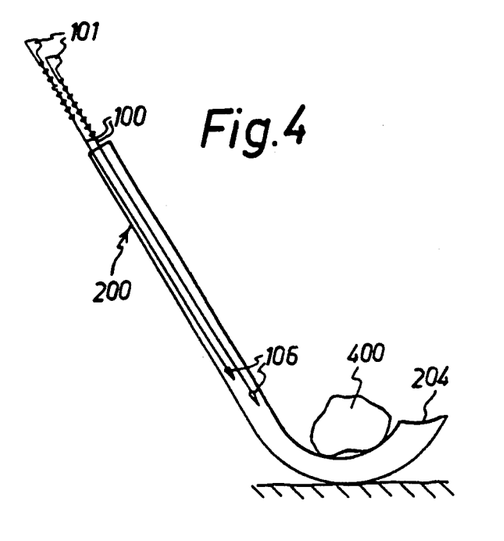

A requisite number (normally two) of occlusion ties 100 are then introduced with their tail portions 105 first into the long leg end 202 of the J-shaped applicator 200. Preferably, the ties 100 are introduced slightly offset with respect to each other, as shown in FIG. 4. However, it is also possible to insert the ties 100 into the long end 202 of the applicator 200 before the latter is passed into the operation area.

Figure 5:
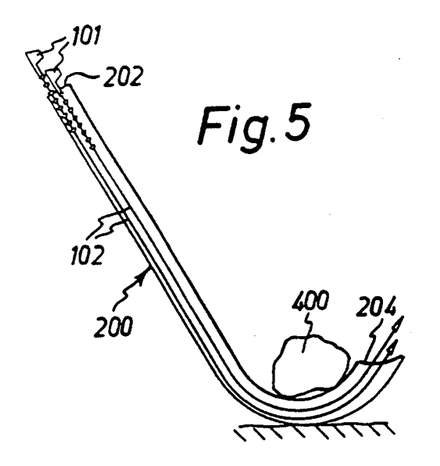

Then, the ties 100 introduced into the long leg 201 are manually guided through the applicator 200 and around the tissue 400, so that the tail portions 105, at least partly, protrude from the short leg end 203 of the applicator, as shown in FIG. 5.

Figure 6:
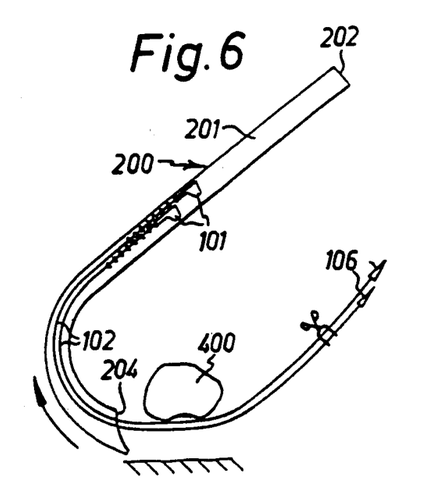

In this position, the tail portions 105 are caught by the fingers or, which is preferred, a suitable instrument, whereupon the applicator 200 is withdrawn as shown in FIG. 6, in order to position the ties 100 in their proper place around the tissue to be occluded and sectioned.

Before the ties 100 are formed into loops, it must be ascertained that they do not cross each other.

Each tie 100 is now formed into a loop by introducing the tail portion 105, held with one hand, into the retaining head 101, held with the other hand, and then pulling the tail portion 105 at the opposite side of the head 101 in order to pass the intermediary portion 104 with the locking cones 107 into the head 101. The loop is thereby automatically locked.

The first tie thus formed into a loop is not immediately cut, but serves as holding means during the formation of the remaining loops. When all the loops have been established the tissue is sectioned between the occlusions, and finally the excess portions of the tongues 101 are cut close to the retaining head.

In the case where the tissue is to be sectioned between forceps, the procedure is similar.

In accordance with an optional feature a loop formed of a tie 100 is tightened with the aid of a separate loop-tightening device 300. Said device 300 is formed with a through opening, which is dimensioned so as to allow the tongue 102, but not the retaining head 101 of the tie 100, to pass therethrough. Preferably, the loop-tightening device 300 is a rigid tube open at two opposite ends, as shown in FIG. 7 The tongue 102 of the tie 100, which has been formed into a loop around the tissue 400, is introduced into a lower end 301 of the tightening tube 300. The loop is tightened by holding the lower end 301 of the tube 300 with one hand against the loop while pulling, with the other hand and in a direction away from the loop, a portion of the tongue 102 which protrudes from the opposite end 302 of the tube 300.

Laparoscopy

Turning to FIGS. 8–14, a second aspect of the invention for use in laparoscopy will now be described.

Generally, laparoscopy is a method for examining and/or for surgically treating the organs and tissues in the abdominal cavity. A requisite number of so-called "ports" (normally in the form of rigid tubes) are passed through the abdominal wall and are directed at different angles towards the examination or operation site in the abdominal cavity. An endoscope is introduced through one of said ports. Another of said ports is connected to a source of carbon dioxide in order to distend the abdominal cavity and thereby obtain better visibility therein. There remaining ports can be used for introducing suitable laparoscopic instruments into the abdominal cavity.

Various metal clamps for occluding blood vessels and tissues containing vessels are presently available. However, for such larger vessels and tissues as in present-day laparoscopic operations (such as intestinal or ovarial resections, etc) no satisfactory method is available for the performing of ligature-like occlusions of tissues on each side of an intended sectioning area.

Now, the occlusion technique according to the invention as described above in connection with laparotomy can be modified, according to a second aspect of the invention, for use in laparoscopy.

Figures 8, 8B:
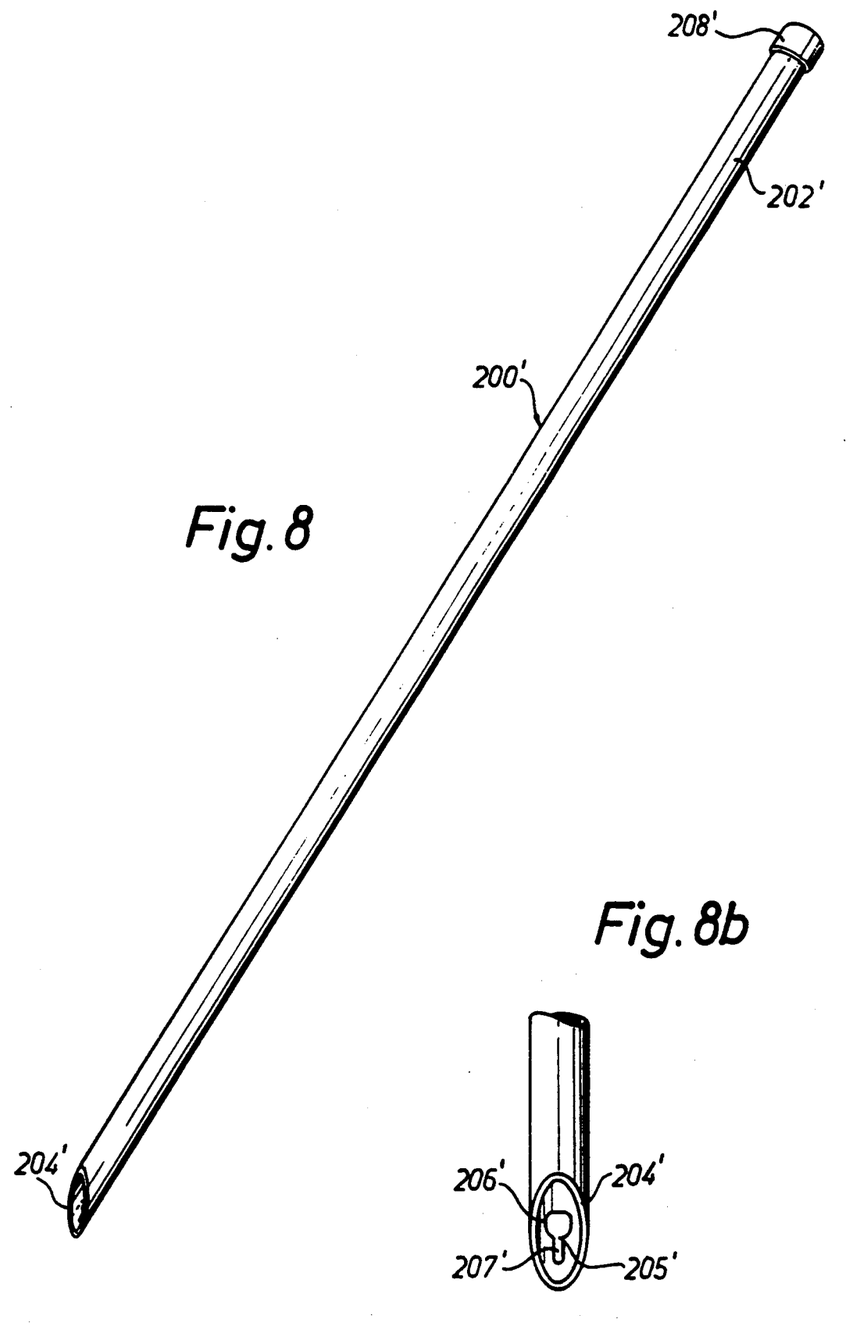
FIG. 8 is a perspective view of an exemplifying tie applicator for use in laparoscopy.

Referring to FIG. 8 an embodiment of an applicator 200' according to the second aspect of the invention for use in laparoscopy consists of a rectilinear (not J-shaped) tube having two opposite open ens 202' and 204'. The occlusion tie 100 for use in laparoscopy will be the same as the one shown in FIG. 1. As for the applicator 200 in FIG. 2, the applicator 200' in FIG. 8 is dimensioned so as to allow the tie 100, including its retaining head 101, to be passed completely through the applicator 200'. However, the rectilinear applicator 200' for use in laparoscopy will normally not have to be dimensioned so as to allow a plurality of ties 100 to be passed through the applicator simultaneously.

The applicator end 204', which is to be inserted through a laparoscopic port and positioned adjacent an operation site within an abdominal cavity, is preferably obliquely cut and spoon-shaped like the applicator end 204 in FIG. 2. Further, this spoon-shaped applicator end 204' is provided with an aperture 205' adapted to receive and catch the insertion tip 106 of a tie 100. The purpose of making the applicator end 204' spoon-shaped is to obtain better accessibility to the aperture 205'. As shown on an enlarged scale in FIG. 8a said aperture 205' is formed of a relatively large opening 206' adapted to receive the insertion tip 106 of a tie 100, and a slot 207' extending from said opening 206' in a direction towards the applicator end 204' and adapted to engage said insertion tip 106.

The opposite applicator end 202', which in use is the outer end, is provided with a membrane 208' of latex rubber or like material. The purpose of the membrane 208' is to prevent gas from leaving the distended abdominal cavity, said gas being introduced at a certain predetermined pressure in the beginning of the laparoscopic procedure. This latex rubber membrane 208' is to be penetrated by the tongue 102 and the head 101 of an occlusion tie 100, as will be described in the following.

Turning now to FIGS. 9-14, successive method steps for the performing of an occlusion during laparoscopy using a tie 100 as shown in FIG. 1, a rectilinear applicator 200' as shown in FIG. 8, and a set of tightening tubes 300' resembling the one shown in FIG. 7, are schematically illustrated.

Throughout FIGS. 9-14 reference numeral 400 indicates the tissue to be occluded and sectioned, 401 indicates the abdominal wall, 402 indicates the abdominal cavity and 403 and 404 indicate two tubular ports passed through the abdominal wall 401 and directed towards the tissue 400.

Figure 9:
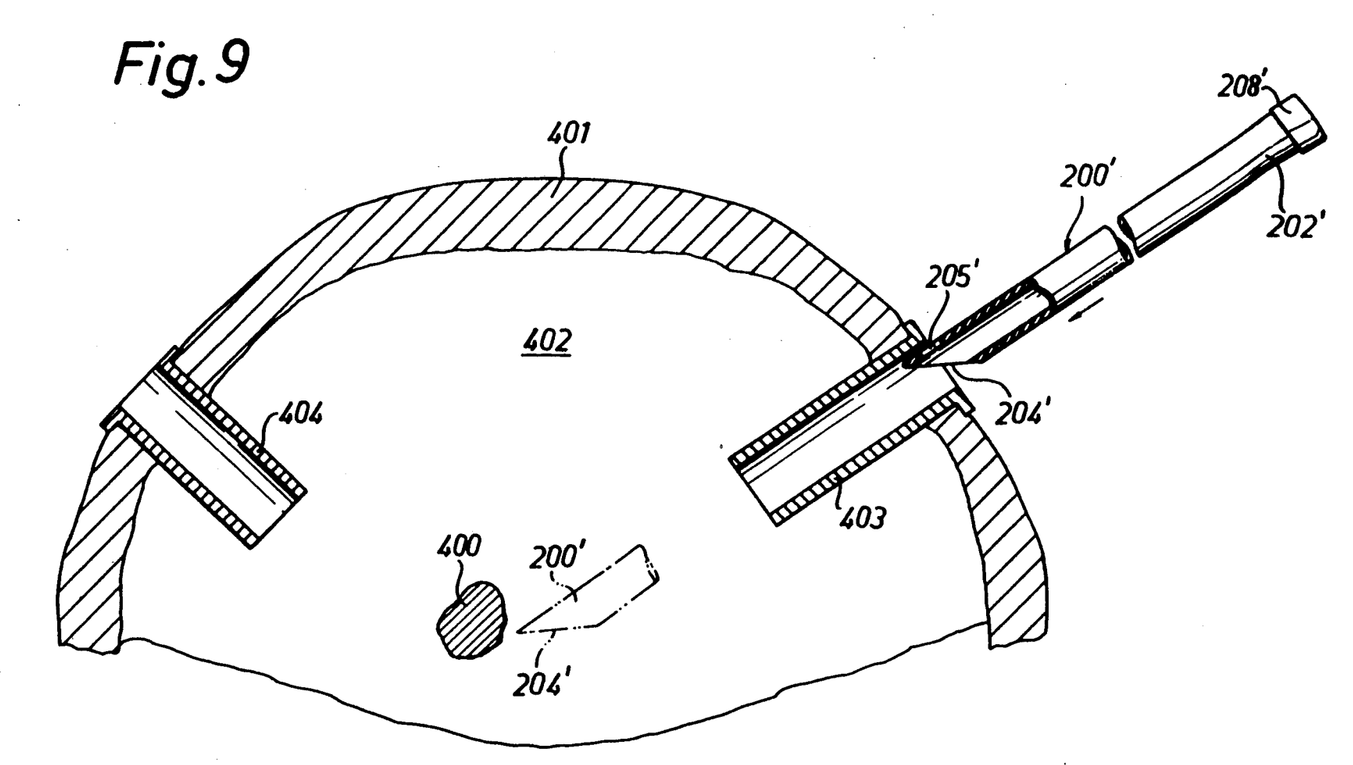
FIGS. 9–14 are simplified views, schematically illustrating successive steps taken during the performance of an occlusion around a tissue during laparoscopy, using a tie as shown in FIG. 1, an applicator as shown in FIG. 8, and tightening tubes as shown in FIGS. 13 and 14.

As a first step shown in FIG. 9 and after performing a free-preparation of the tissue 400 to be occluded and sectioned, the applicator 200' is introduced with its spoon-shaped end 204' first through one (403) of the laparoscopic ports. As indicated by dashed lines in FIG. 9, the applicator end 204' is to be positioned in the close proximity of the tissue 400. This first step, as well as the following steps to be taken, can be supervised by means of an endoscope, which is introduced through another laparoscopic part (not shown) and connected to a monitor (not shown). The laparoscopic ports, such as ports 403 and 404, are (as known to a man skilled in the art) provided with latex rubber membranes (not shown), which are to be penetrated by different instruments and the purpose of which is to prevent gas leakage from the abdominal cavity 402. Thus, there is provided a gas seal between the port 403 and the applicator 200' passed therethrough.

Figure 10:
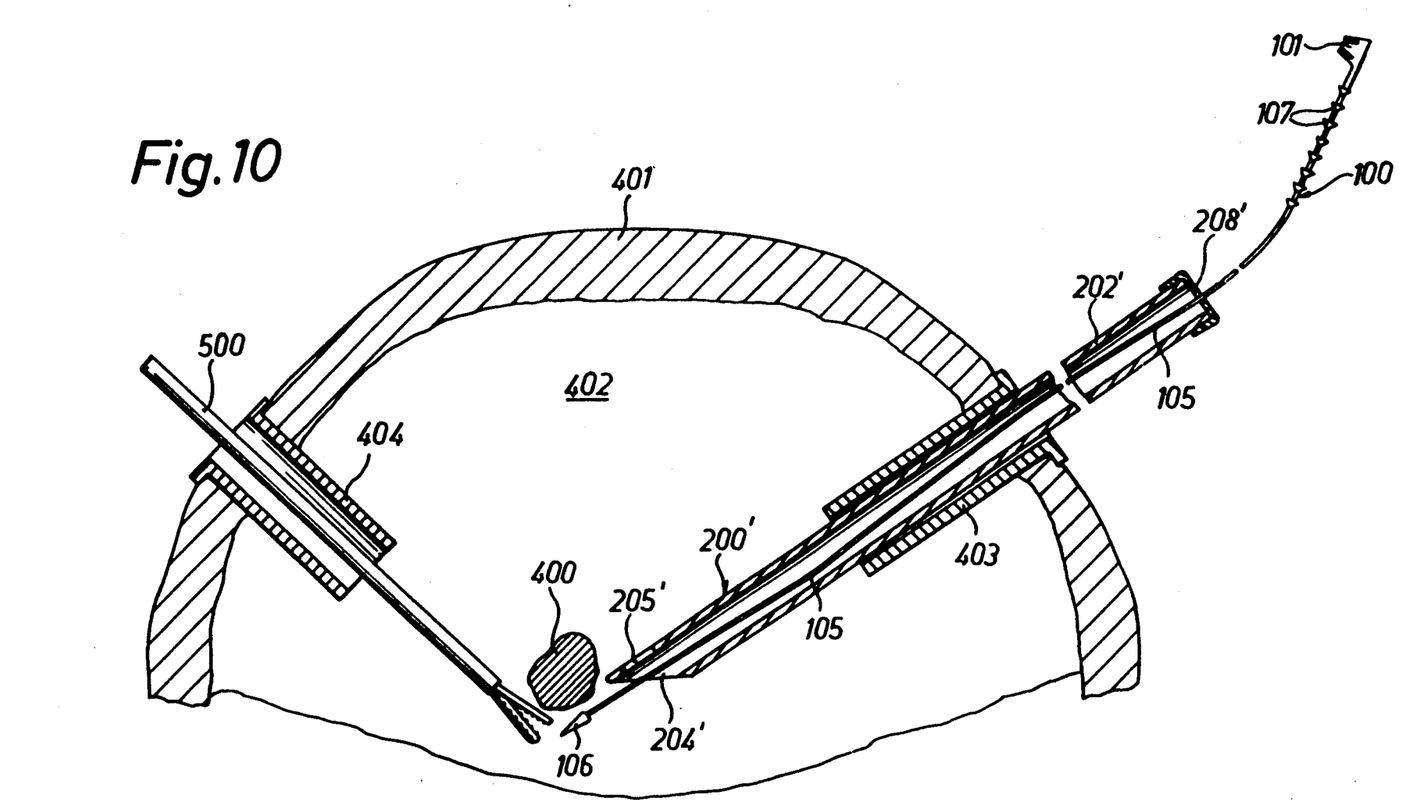

As a second step shown in FIG. 10, a tie 100 is introduced with its tail portion 105 first into the outer applicator end 202', whereby the applicator membrane 208' is penetrated. The tie 100 is introduced to such an extent that its tail portion 105 protrude, at least partly, from the spoon-shaped end 204' of the applicator 200'. At this stage, the head 101 of the tie 100 is still visible outside the applicator 200'. The protruding tail portion 105 is then caught by a suitable laparoscopic instrument 500, such as a pair of forceps, which has been introduced through another (404) of said laparoscopic ports and been passed under the tissue 400.

Figure 11:
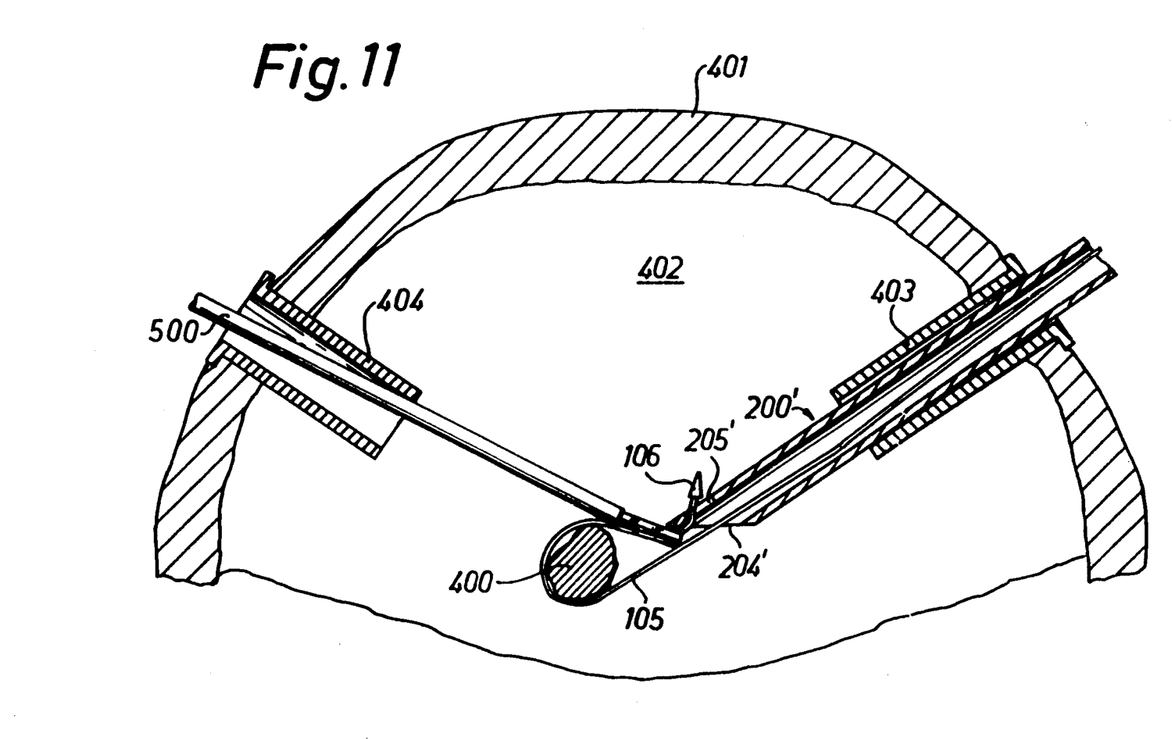

As a third step shown in FIG. 11, the tail portion 105 caught by the forceps 500 is drawn out of the applicator end 204, around the tissue 400 and is inserted with its tip 106 into the aperture 205' which is formed in the applicator end 204'. The arrow-like tip 106 is passed through the relatively large opening 206' of the aperture 205' in order to thereafter slide down into the slot 207' to be caught.

Figure 12:
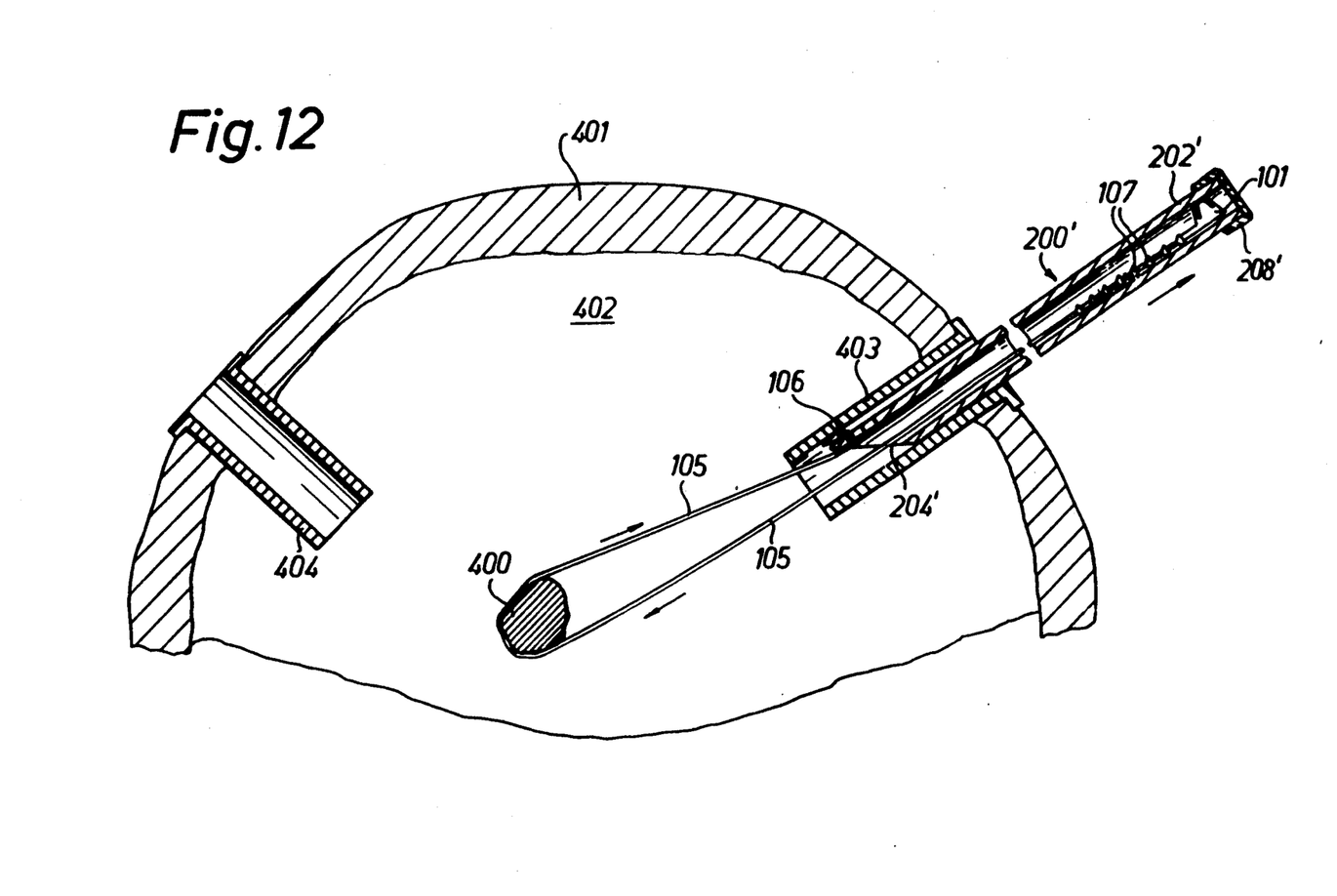
Figure 13:
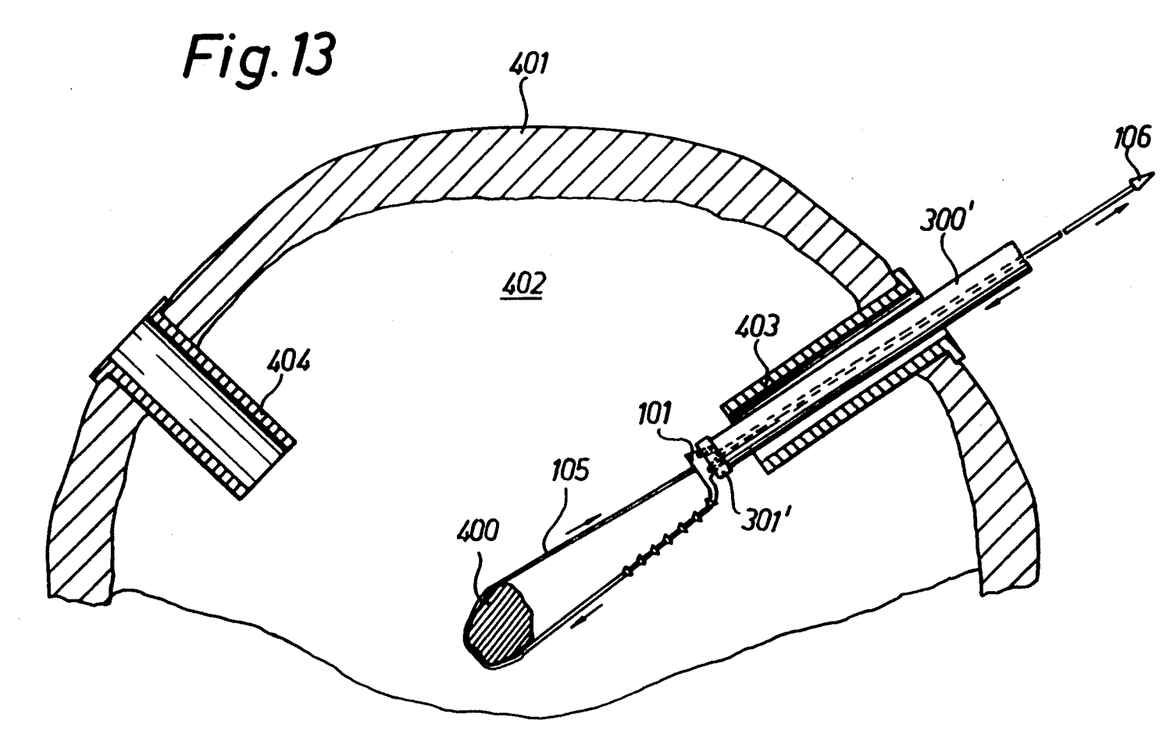

As a fourth step shown in FIG. 12, the applicator 200' is extracted from the abdominal cavity 402, whereby the tail portion 105 of the tie 100 is pulled outwards through the port 403, while the retaining head 101 of the tie 100 is simultaneously pulled inwards through the port 403, i.e. the tie 100 lies double in the applicator 200'. Obviously, the retaining head 101 of the tie 100 will pass through the applicator 200', as indicated in FIG. 13. At this stage of the occlusion procedure the thread-shaped intermediary portion 104 of the tie 100 will slide in a non-locked loop path around the tissue 400.

Figure 14:
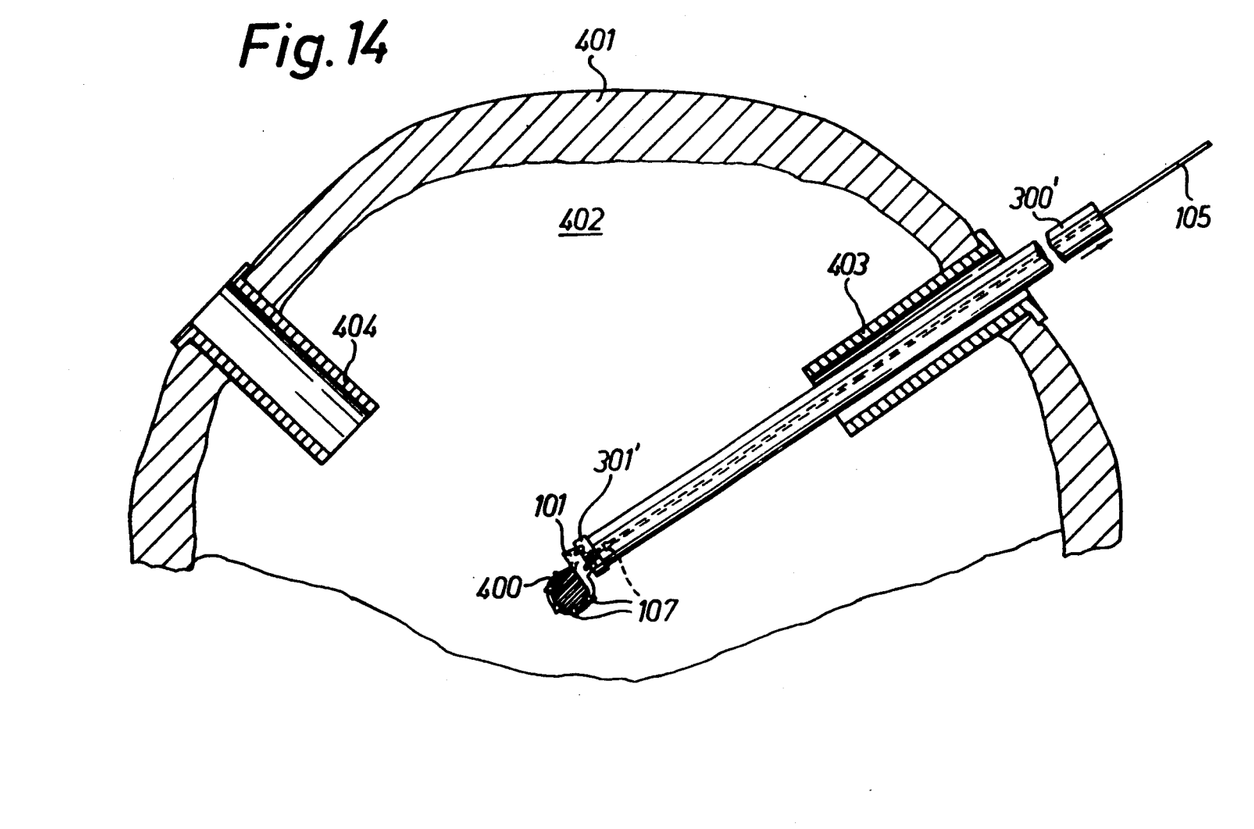

As a fifth step shown in FIGS. 13 and 14 and after the applicator 200' has been completely extracted and removed, the two ends of the tie 100 which are now visible are grasped by hand in order to form the tie 100 into a closed loop. As in the first aspect of the invention described above, this is done by introducing the tail portion 105, held with one hand, into the retaining head 101, held with the other hand, and then pulling the tail portion 105 at the opposite side of the head 101. Thereafter, the retaining head 101 is manually moved down as far as possible towards the outer end of port 403. The retaining head 101 is pushed further down through the port 403 towards the tissue 400 by means of tightening tubes 300' of increasing length (the tube 300' in FIG. 13 is shorter than the one in FIG. 14). The function of the tightening tubes 300' is basically the same as for the tightening tube 300 shown in FIG. 7 and will therefore not be repeated.

When the retaining head 101 has been pushed inwards to a certain extent, it becomes visible inside the port 403 by means of the endoscope. A suitable number of the locking cones 107 can then be pulled through the retaining head 101 to accomplish a locked and suitably firm occlusion loop around the tissue 400.

However, the tightening tubes 300' for use in laparoscopy differ from the tube 300 for use in laparotomy in the following two respects.

First, since a substantial part of the length of the tie 100 will be located within the port 403 and within the abdominal cavity 402 and therefore is not manually accessible as in the laparotomy case, it would normally not be sufficient to use a single tightening tube of a given length, as in FIG. 7. Instead, a set of two or more tightening tubes 300' of increasing length will normally have to be used for performing a complete tightening of the loop around the tissue 400 inside the abdominal cavity 402.

Second, the tightening tubes 300' for use in laparoscopy will be provided with gas sealing membranes 301' at one end, preferably the end which in use is the inner end of the tightening tube 300'.

As a final step in the occlusion procedure and after the firm occluding loop has been established around the tissue 400, the excess portion of the tongue 102 is cut close to the retaining head 101.

A second occlusion loop may be formed in the same way on the other side of the intended sectioning area of the tissue 400, whereupon the tissue 400 may be sectioned between the occlusions by means of suitable laparoscopic instrument.

In an alternative to the laparoscopic occlusion procedure described above in connection with FIGS. 9–14, the step of withdrawing the tail portion 105 of the tie 100 from the abdominal cavity 403 can be performed by other means than by using the tip catching aperture 205' in the applicator end 204' (FIG. 12). Thus, it is possible to remove the applicator 200' immediately after the tail portion 105 has been caught by the forceps 500 (FIG. 10). A suitable instrument, such as a second pair of forceps, can then be inserted, e.g. through the "applicator port" 403, to grasp the tail portion 105, the first pair of forceps 500 being released therefrom. As in FIG. 11, the tie 100 would lie doubled in the port 403 when the tail portion 105 is pulled outwards and the retaining-head 101 is simultaneously pulled inwards.

What is claimed is:

1. A method for performing a surgical occlusion on human or animal tissue, said method comprising the following steps:
    positioning a tubular applicator having a first and a second open applicator end, with said first applicator end adjacent the tissue;
    introducing into said applicator at least one elongated and flexible bundle-strap type occlusion tie having an apertured retaining head and a tongue which extends from said head and is formed integrally therewith;
    catching a portion of said tie protruding from said first applicator end and arranging the tie around the tissue; and
    after said step of arranging the tie around the tissue, forming the tie into a closed occlusion loop around the tissue by inserting and pulling the tongue through the retaining head.

2. A method as claimed in claim 1, wherein said tie is introduced into the applicator with its tongue directed towards the tissue.

3. A method as claimed in claim 1, further comprising the following steps, performed after said step of forming the tie into a closed loop:
    introducing the tongue into a loop-tightening device formed with a through opening dimensioned so as to allow the tongue, but not the retaining head of said tie, to pass therethrough; and then
    tightening said loop by holding the loop-tightening device against the loop while pulling, in a direction away from the tissue, a portion of said tongue which protrudes from said through opening of the loop-tightening device.

4. A method as claimed in claim 1 for use in laparotomy or thoracotomy, said tubular applicator being substantially J-shaped and having a short leg at said first applicator end and a long leg at said second applicator end, wherein:
    said step of positioning the first applicator end adjacent the tissue comprises the step of passing around the tissue the short leg by manual handling of the long leg; and
    said step of catching a tie portion and arranging the tie around the tissue comprises the steps of catching and holding back said tie portion which is protruding from the short leg of the J-shaped applicator, and simultaneously withdrawing the J-shaped applicator by manual handling of the long leg, whereby the tie is arranged around the tissue.

5. A method as claimed in claim 4 for use in laparotomy or thoracotomy, wherein a plurality of said occlusion ties are introduced substantially simultaneously into said J-shaped applicator in order to be positioned substantially simultaneously around the tissue when the J-shaped applicator is withdrawn.

6. A method as claimed in claim 1 for use in laparoscopy, said tubular applicator being substantially rectilinear, wherein:
    said step of positioning the first end of the applicator adjacent the tissue comprises the step of introducing the rectilinear applicator, with the first applicator nd first, through a laparoscopic port in order to position the first applicator end adjacent the tissue; and
    said step of catching a tie portion and arranging the tie around the tissue is performed by means of a laparoscopic instrument which is introduced through a further laparoscopic port.

7. A method as claimed in claim 6 for use in laparoscopy, said rectilinear applicator presenting a lateral tie engaging aperture in close proximity to the first applicator end, further comprising the following steps, performed after the step of arranging the tie around the tissue but before the step of forming the tie into a closed loop:
    introducing by means of said laparoscopic instrument an end portion of the tongue of the tie into said tie engaging aperture at the first applicator end;
    withdrawing the applicator from said laparoscopic port, whereby the applicator entrains said end portion of the tongue of the tie to the outside of said laparoscopic port, whereupon the tie can be formed into said closed loop.

8. A method as claimed in claim 6 for use in laparoscopy, further comprising the following steps, performed after said step of forming the tie into a closed loop:
introducing the tongue into a rigid loop-tightening tube dimensioned so as to allow the tongue, but not the retaining head of said tie, to pass therethrough; and then
tightening said loop by holding the loop-tightening tube against the loop while pulling, in a direction away from the tissue, a portion of said tongue which protrudes from said loop-tightening tube, and while successively introducing the loop-tightening tube through said laparoscopic port.

9. A kit for performing a surgical occlusion on human tissue during laparotomy or thoracotomy, said kit comprising in combination:
a) at least one elongated and flexible, bundle-strap type, occlusion ties, each tie having an apertured retaining head and a tongue which extends from said head and is formed integrally therewith; and
b) a tubular, substantially J-shaped applicator having a long leg with an open applicator end, and a short leg with an open applicator end;
said long leg being adapted to receive at least one of said ties, and said short leg being adapted to be passed around the tissue by manual handling of said long leg; and
said applicator being dimensioned so as to allow the whole tie to be passed through the applicator and out therefrom at the short leg end in order to position the tie in its proper place around the tissue when the applicator is withdrawn, whereupon the tie can be closed into a locked occlusion loop around the tissue by passing the tongue through the retaining head.

10. A kit as claimed in claim 9 for use in laparotomy or thoracotomy, wherein said applicator is dimensioned so as to allow a plurality of ties to be passed substantially simultaneously through the applicator in order to position said plurality of ties substantially simultaneously around the tissue when the applicator is withdrawn.

11. A kit as claimed in claim 9 for use in laparotomy or thoracotomy, further comprising:
c) a loop-tightening device having a through opening which is dimensioned so as to allow said tongue, but not the retaining head of said tie, to pass therethrough.

12. A kit as claimed in claim 11 for use in laparotomy or thoracotomy, wherein said loop-tightening device is a rigid tube which is open at two opposite ends.

13. A kit as claimed in claim 9 for use in laparotomy or thoracotomy, wherein the length of each tie exceeds the overall length of said applicator.

14. A kit as claimed in claim 9 for use in laparotomy or thoracotomy, wherein said tongue, starting from the retaining head, comprises a relatively short head portion, an intermediary portion and a relatively long tail portion, said intermediary portion being provided with locking elements formed integrally with the tongue and adapted to engage locking means of said retaining head, whereas said head portion and said tail portion of the tongue are not provided with such locking elements.

15. A kit as claimed in claim 9 for use in laparotomy or thoracotomy, wherein the tongue of each tie is substantially thread-shaped so as to be flexible in all directions relative to a main axis of said tongue.

16. A kit for performing a surgical occlusion on human or animal tissue during laparoscopy, said kit comprising in combination:
a) at least one elongated and flexible, bundle strap type, occlusion tie, said tie having an apertured retaining head and a tongue which extends from said head and is formed integrally therewith;
b) a tubular, substantially rectilinear applicator having a first and a second open applicator end, said applicator being adapted to be introduced, with the first applicator end first, through a laparoscopic port in order to position the first applicator end in the close proximity of the tissue; and said applicator being dimensioned so as to allow the whole tie, preferably with its tongue first, to be passed through the applicator and out therefrom at said first applicator end,
said tongue being adapted to be caught by means of a suitable laparoscopic instrument at said first applicator end adjacent the tissue and, by means of said instrument, arranged around the tissue, whereupon said tongue is to be pulled out through said laparoscopic port, on the outside of which the tie is to be formed into a closed loop by passing the tongue through the retaining head; and
c) at least one substantially rectilinear loop-tightening tube dimensioned so as to allow the tongue, but not the retaining head of said tie, to pass therethrough, whereby said closed loop can be tightened around the tissue by pulling the tongue of the tie through the loop-tightening tube, after the tie has been formed into said closed loop, and then successively introducing the loop-tightening tube into said laparoscopic port while pulling a portion of the tongue which protrudes from an outer end of the loop-tightening tube.

17. A kit as claimed in claim 16 for use in laparoscopy, wherein the length of the tie exceeds the overall length of said applicator.

18. A kit as claimed in claim 16 for use in laparoscopy, wherein said tongue, starting from the retaining head, comprises a relatively short head portion, an intermediary portion and a relatively long tail portion, said intermediary portion being provided with locking elements formed integrally with the tongue and adapted to engage locking means of said retaining head, whereas said head portion and said tail portion of the tongue are not provided with such locking elements.

19. A kit as claimed in claim 16 for use in laparoscopy, wherein the tongue of the tie is substantially thread-shaped so as to be flexible in all directions relative to the main axis of said tongue.

20. A kit as claimed in claim 16 for use in laparoscopy, wherein said applicator is provided with a gas sealing membrane, which is arranged over the second applicator end and which is adapted to be penetrated by said tie.

21. A kit as claimed in claim 16 for use in laparoscopy, wherein said at least one loop-tightening tube is provided with a gas sealing membrane which is preferably arranged over a loop-engaging end of said tube and which is adapted to be penetrated by said tie.

22. A kit as claimed in claim 16 for use in laparoscopy, wherein said applicator is provided with an lateral tie-engaging aperture in the close proximity of the first applicator end, said aperture being adapted to receive an end portion of the tongue, after the latter has been arranged around the tissue by means of said laparoscopic instrument, whereby withdrawal of the applicator from said laparoscopic port will move said end portion of the tongue to the outside of said laparoscopic port, whereupon the tie can be formed into said closed loop.

* * * * *

UNITED STATES PATENT AND TRADEMARK OFFICE
CERTIFICATE OF CORRECTION

PATENT NO. : 5,207,694
DATED : May 4, 1993
INVENTOR(S) : Albert Broomé

It is certified that error appears in the above-identified patent and that said Letters Patent is hereby corrected as shown below:

Column 9:
In claim 9, line 1, after "human", insert --or animal--.

Signed and Sealed this

Twenty-fifth Day of January, 1994

Attest:

BRUCE LEHMAN

Attesting Officer    Commissioner of Patents and Trademarks